US00PP13577P2

(12) United States Plant Patent
van Schie

(10) Patent No.: US PP13,577 P2
(45) Date of Patent: Feb. 18, 2003

(54) GUZMANIA PLANT NAMED 'DEPLADIA'

(76) Inventor: Hubertus L. van Schie, Deltsestraatweg 15B, 2645 CA, Delfgauw (NL)

( * ) Notice: Subject to any disclaimer, the term of this patent is extended or adjusted under 35 U.S.C. 154(b) by 0 days.

(21) Appl. No.: 10/024,193

(22) Filed: Dec. 21, 2001

(30) Foreign Application Priority Data

Aug. 20, 2001 (EP) ..... 2001/1174

(51) Int. Cl.[7] ..... A01H 5/00
(52) U.S. Cl. ..... Plt./371
(58) Field of Search ..... Plt./371

*Primary Examiner*—Kent L. Bell
(74) *Attorney, Agent, or Firm*—Foley & Lardner

(57) ABSTRACT

A new and distinct Guzmania plant named 'Depladia' characterized by compact plant shape; short, green leaves; compact flower shape and yellow inflorescences with green tips and orange-red at the very tips of the apex.

2 Drawing Sheets

LATIN NAME OF THE GENUS AND SPECIES OF THE PLANT CLAIMED

Guzmania hybrid.

VARIETY DENOMINATION

'Depladia'.

BACKGROUND OF THE INVENTION

The present invention comprises a new and distinct cultivar of Guzmania plant, hereinafter referred to by the cultivar name 'Depladia'. The genus Guzmania is a member of the family Bromeliaceae.

Guzmania comprise a genus of over 100 species of herbaceous evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from the yellow through orange but may also include flame red and red-purple. White or yellow, tubular, three petalled flowers may also appear on a stem or within the leaf rosette but are usually short lived.

Guzmania may be advantageously grown as potted plants for greenhouse or home use. Desirably the plants are shaded from direct sunlight during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in an appropriate soil or bark mixture.

The new cultivar 'Depladia' was discovered by the inventor Hubertus L. van Schie, as a naturally occurring whole plant mutation of Guzmania 'Hilda' (unpatented) in 1995 in Delfgauw, The Netherlands.

The new cultivar was asexually propagated by taking cuttings by the inventor in Delfgauw, The Netherlands in 1995. Asexual propagation by tissue culture was initiated in 1999 by Deroose Plants, Evergem, Belgium. Continuous asexual propagation has demonstrated that the combination of characteristics as herein disclosed for the new cultivar 'Depladia' are firmly fixed and are retained through successive generations of asexual reproduction. The new cultivar reproduces true to type.

BRIEF DESCRIPTION OF THE INVENTION

The following traits have been repeatedly observed and are determined to be basic characteristics of 'Depladia' which in combination distinguish this Guzmania as a new and distinct cultivar:

1. Compact plant shape.

2. Yellow inflorescence with green tips and orange-red at the very tip of the apexs; and 3. Relatively short green leaves.

'Depladia' has not been observed under all possible environmental conditions. The phenotype of the new cultivar may vary significantly with variations in environment such as temperature, light intensity, and day length without any change in genotype.

Of the many commercial cultivars known to the present inventor, the most similar in comparison to 'Depladia' is the parental cultivar 'Hilda', which is characterized by its yellow inflorescence. In comparison to 'Hilda', the plant shape of 'Depladia' is more compact and the inflorescence of 'Depladia' is shorter.

BRIEF DESCRIPTION OF THE DRAWINGS

The accompanying photographic drawings show a 19-month-old 'Depladia' plant following growth under appropriate growing conditions, with colors being as true as possible with illustrations of this type.

The drawing at the top of sheet one depicts a close-up view of a typical inflorescence of 'Depladia'.

The drawing at the bottom of sheet one depicts a side view of a typical plant of 'Depladia'.

The drawing at the top of sheet two depicts a side view of 'Hilda' (left) and 'Depladia' (right).

The drawing at the bottom of sheet two depicts a close-up view of 'Hilda' (left) and 'Depladia' (right).

DETAILED BOTANICAL DESCRIPTION

The following observations, measurements and values describe 19 month old plants grown in 10.5 cm pots in Delfgauw, The Netherlands, under greenhouse conditions which closely approximate those generally used in horticultural practice. Color references are made to The Royal Horticultural Society Colour Chart (R.H.S.), except where general colors of ordinary significance are used.

Propagation: Tissue culture.

Plant:

*Form.*—Upright, leaves in basal rosette.

*Height.*—Average 37 cm.

*Diameter.*—Average 60 cm.

*Growth habit.*—Upright, growth moderate.

*Time it takes to produce a mature flowering plant.*—2 years.

Foliage:

*Size.*—Leaves have an average length of 33 cm and an average width of 4.1 cm (measured at the middle of a leaf).

*Shape.*—Linear, tips acute.

*Margin.*—Entire.

*Surface texture.*—Smooth, glossy.

*Color.*—Leaf color upper side green to yellow-green; in between RHS 137 A and RHS 147 A. Leaf color under side yellow-green; RHS 146 A, sometimes striped lengthways greyed orange; RHS 176 B.

Bracts:

*General shape/arrangement.*—Lanceolate, arranged alternately, tips bent downward in an average angle of 30° to 50°.

*Scape bracts.*—Number: Average 6. Length: Average 14 cm. Width: Average 3.6 cm. Margin: Entire. Apex: Acute. Color: Upper side green RHS 137A; base yellow-green RHS 153C; under side upper half green RHS 137B with yellow-green base RHS 144A. Texture: Smooth, glossy.

*Primary bracts.*—Number: Average 11. Length: Average 11 cm. Width: Average 3.8 cm. Margin: Entire. Apex: Acute. Color: Upper side yellow-green to yellow-orange between RHS 153C and 14A, with green tips between RHS 143A and RHS 143B and orange-red at the tip of the apex RHS 178A; under side yellow-green RHS 153C with green tips RHS 143C with orange-red at the tip of the apex between RHS 178A and RHS 178B. Texture: Smooth.

*Floral bracts.*—Number: Average 9. Length: Average 9 cm. Width: Average 2.5 cm. Margin: Entire. Apex: Acute. Color: Upper side yellow-green to yellow-orange between RHS 153C and 14A (both surfaces). Texture: Smooth.

Inflorescence:

*Borne.*—Solitary upright inflorescence.

*Individual flowers.*—Quantity of flowers: 5 per inflorescence. Perianth: 1 large petal, lanceolate, folded, average length 5 cm, average width 7 mm, outer surface color yellow-green RHS 153A, with yellow-green base RHS 150D to green-white RHS 157A; inner surface yellow-green between RHS 153C and RHS 153D, with yellow-green base RHS 150D; the rest of the perianth consists of 3 petals, lanceolate, average length 3.8 cm, average width 5 mm, yellow-orange in color between RHS 21A and RHS 21B, with yellow-green base RHS 150D.

*Time of blooming.*—Summer.

*Duration of inflorescence.*—Up to 6 months.

Reproductive organs:

*Stamen.*—6, average length 2.7 cm.

*Filaments.*—Average length 2.3 cm, yellow-green in color RHS 150D.

*Anthers.*—Average length 4 mm, basifixed, yellow-green in color RHS 150D.

*Pollen.*—Small quantity, yellow RHS 4C.

*Style.*—Average length 2.7 cm, yellow RHS 6B.

*Stigma.*—Average length 2 mm, yellow RHS 6B.

*Ovary.*—Oblong, average length 8 mm, average width 3 mm, yellow-green in color RHS 145C.

Roots: Thin, very well-branched, strong to moderately strong, color greyed-orange RHS 165 A.

Seed characteristics: No observations to date.

Disease/pest resistance/susceptibility: 'Depladia' is no more resistant or susceptible to diseases and pests than other Guzmania varieties.

I claim:

1. A new and distinct Guzmania plant named 'Depladia' as illustrated and described herein.

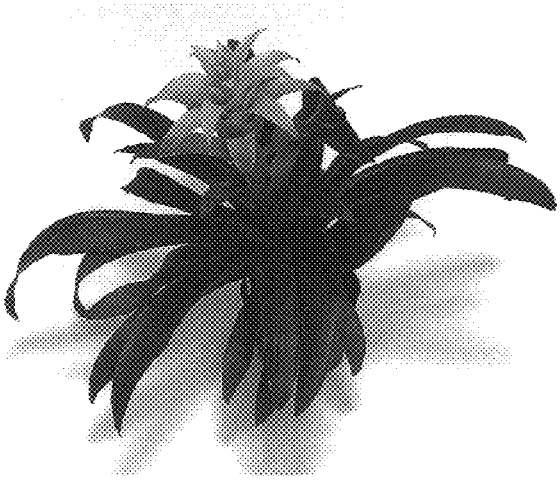
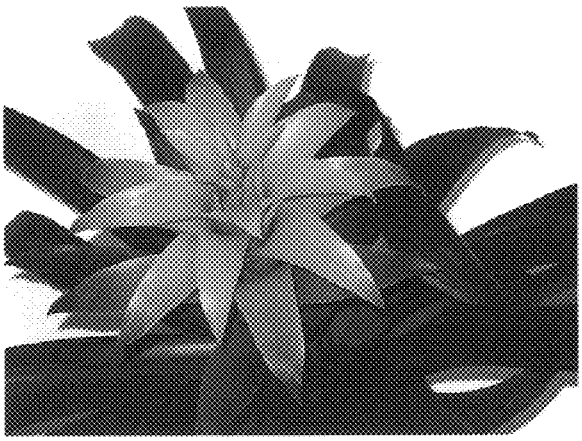

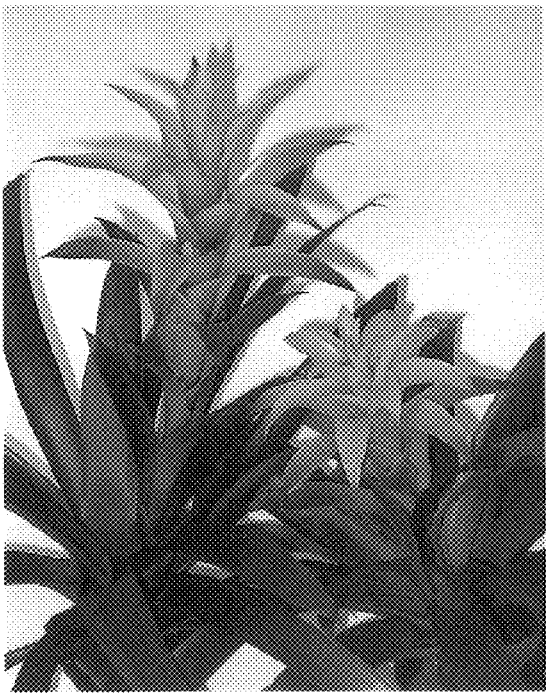
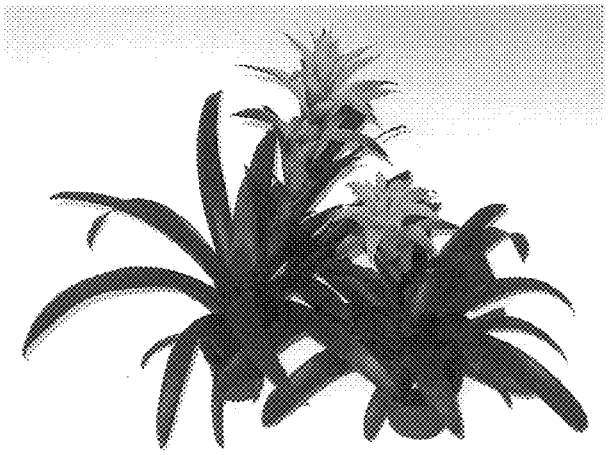

* * * * *